(12) United States Patent
Baldus et al.

(10) Patent No.: US 9,974,908 B2
(45) Date of Patent: May 22, 2018

(54) FALL DETECTORS AND A METHOD OF DETECTING FALLS

(75) Inventors: Heribert Baldus, Eindhoven (NL); Jacob Roger Haartsen, Eindhoven (NL); Stephan Schlumbohm, Frankfurt am Main (DE); Ronald Dekker, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 766 days.

(21) Appl. No.: 13/379,051

(22) PCT Filed: Dec. 17, 2009

(86) PCT No.: PCT/IB2009/055810
§ 371 (c)(1),
(2), (4) Date: Dec. 20, 2011

(87) PCT Pub. No.: WO2011/010191
PCT Pub. Date: Jan. 27, 2011

(65) Prior Publication Data
US 2012/0109575 A1    May 3, 2012

(30) Foreign Application Priority Data
Jul. 22, 2009  (EP) .................................. 09166078

(51) Int. Cl.
*G06F 15/00* (2006.01)
*G01P 15/00* (2006.01)
(Continued)

(52) U.S. Cl.
CPC .......... *A61M 11/005* (2013.01); *A61B 5/1117* (2013.01); *A61B 5/681* (2013.01);
(Continued)

(58) Field of Classification Search
CPC .... A61B 2562/0219; A61B 2562/0271; A61B 5/1117; A61B 5/681; A61B 5/6831
(Continued)

(56) References Cited

U.S. PATENT DOCUMENTS

| | | | |
|---|---|---|---|
| 4,637,736 A | 1/1987 | Andeen et al. | |
| 5,567,877 A * | 10/1996 | Nishio | G01P 9/00 73/204.25 |

(Continued)

FOREIGN PATENT DOCUMENTS

| | | |
|---|---|---|
| EP | 1128349 A1 | 8/2001 |
| EP | 1566782 A1 | 8/2005 |

(Continued)

OTHER PUBLICATIONS

Chen et al., "A Novel Two-Axis CMOS Accelerometer Based on Thermal Convection", IEEE Transactions on Instrumentation and Measurement, vol. 57, No. 8, Aug. 2008, pp. 1572-1577.*
(Continued)

*Primary Examiner* — John H Le

(57) ABSTRACT

There is provided a fall detector for detecting falls of a user or an object to which the fall detector is attached, characterized in that the fall detector comprises an air flow sensor for providing measurements indicative of vertical velocity and/or changes in altitude of the fall detector.

14 Claims, 9 Drawing Sheets

(51) Int. Cl.
*A61M 11/00* (2006.01)
*A61M 16/18* (2006.01)
*A61M 16/10* (2006.01)
*A61B 5/11* (2006.01)
*A61B 5/00* (2006.01)
*A61M 15/00* (2006.01)
*G01P 5/10* (2006.01)
*G01P 5/12* (2006.01)
*G01P 13/00* (2006.01)
*G08B 21/04* (2006.01)
*A61M 11/04* (2006.01)
*A61M 5/168* (2006.01)
*A61M 16/00* (2006.01)

(52) U.S. Cl.
CPC ......... *A61B 5/6831* (2013.01); *A61M 11/003* (2014.02); *A61M 11/042* (2014.02); *A61M 15/00* (2013.01); *A61M 16/0003* (2014.02); *A61M 16/104* (2013.01); *A61M 16/18* (2013.01); *G01P 5/10* (2013.01); *G01P 5/12* (2013.01); *G01P 13/006* (2013.01); *G08B 21/0446* (2013.01); *A61B 2562/0219* (2013.01); *A61B 2562/0271* (2013.01); *A61M 5/16886* (2013.01); *A61M 2016/003* (2013.01); *A61M 2016/0021* (2013.01); *A61M 2016/0027* (2013.01); *A61M 2205/332* (2013.01); *A61M 2205/3334* (2013.01); *A61M 2205/3368* (2013.01); *A61M 2205/3375* (2013.01); *A61M 2205/50* (2013.01); *A61M 2205/82* (2013.01); *Y10T 29/49117* (2015.01); *Y10T 29/49128* (2015.01)

(58) Field of Classification Search
USPC ....... 702/141, 92, 136, 138, 142; 73/114.34; 123/391; 600/595
See application file for complete search history.

(56) References Cited

U.S. PATENT DOCUMENTS

| | | | |
|---|---|---|---|
| 5,825,487 A * | 10/1998 | Felbinger | G01N 15/1404 250/576 |
| 6,658,292 B2 | 12/2003 | Kroll et al. | |
| 6,746,932 B2 | 6/2004 | Pannek | |
| 7,255,001 B1 | 8/2007 | Davis et al. | |
| 7,742,894 B2 | 6/2010 | Chen et al. | |
| 2004/0013158 A1 | 1/2004 | Bazhenov | |
| 2006/0049950 A1 | 3/2006 | Lockhart | |
| 2007/0251292 A1 | 11/2007 | Beck et al. | |
| 2007/0265533 A1 | 11/2007 | Tran | |
| 2008/0021676 A1 | 1/2008 | Vock et al. | |
| 2008/0133277 A1 * | 6/2008 | Jang | A61B 5/0002 705/3 |
| 2008/0234935 A1 | 9/2008 | Wolf et al. | |
| 2009/0064968 A1 * | 3/2009 | Shoyama | G01F 5/00 123/391 |
| 2009/0322540 A1 * | 12/2009 | Richardson et al. | 340/573.7 |
| 2010/0052896 A1 * | 3/2010 | Goodman | G08B 21/0446 340/539.11 |
| 2010/0286567 A1 * | 11/2010 | Wolfe et al. | 600/587 |
| 2012/0101411 A1 * | 4/2012 | Hausdorff | A61B 5/1117 600/595 |
| 2014/0156216 A1 * | 6/2014 | Ten Kate | A61B 5/1117 702/142 |

FOREIGN PATENT DOCUMENTS

| | | | |
|---|---|---|---|
| EP | 1642248 B1 * | 3/2007 | |
| EP | 1779772 A1 | 5/2007 | |
| FR | 2760116 A1 | 8/1998 | |
| FR | 2829862 A1 | 3/2003 | |
| JP | 2008032521 A | 2/2008 | |
| JP | 2009191709 A | 8/2009 | |
| RU | 2341775 C1 | 12/2008 | |
| SU | 877440 A1 | 10/1981 | |
| SU | 1569858 A1 | 6/1990 | |
| TW | 200737056 | 10/2007 | |
| TW | 200912814 A | 3/2009 | |
| TW | 200929088 A | 7/2009 | |
| WO | 2009101566 A1 | 8/2009 | |
| WO | 2011010260 A1 | 1/2011 | |

OTHER PUBLICATIONS

Bourke, A.K., O'Donovan, K.J., Nelson, J., Olaighin, G.M., "Fall-Detection Through Vertical Velocity Thresholding Using a Tri-axial Accelerometer Characterized Using an Optical Motion-Capture System", 3oth Annual International IEEE EMBS Conference, Aug. 20-24, 2008, vol. 2008, pp. 2832-2835.

Wu, G.A., Hue, S.B., "Portable Preimpact Fall Detector With Inertial Sensors", IEEE Transactions on Neural Systems and Rehabilitation Engineering, vol. 16, No. 2, Apr. 2008, pp. 178-183.

Kim et al: "Measurement of Flow Direction and Velocity Using a Micromachined Flow Sensor"; Sensors and Actuatiors A 114 (2004), pp. 312-218.

Wei et al: "Structure and Signal Processing of the Gas Pendulum Level Posture Sensor"; Electronic Components and Materials, Aug. 2005, vol. 24, No. 8, pp. 1-3.

LV Yaojie: "FEM Analysis of Micromachined Airflow Accelerometer's Sensitive Mechanism"; Electronic Components and Materials, Oct. 2007, vol. 26, No. 10, pp. 64-66.

Piao Linhua et al: "Research on Airflow Level Posture Sensor for Restraining Acceleration Interference"; Piezoelectircs & Acoustooptics, Dec. 2006, vol. 28, No. 6, pp. 659-661.

* cited by examiner

FALL DETECTORS AND A METHOD OF DETECTING FALLS

TECHNICAL FIELD OF THE INVENTION

The invention relates to a fall detector and a method of detecting falls, and in particular to a fall detector and method that uses multiple sensors for detecting falls. The invention also relates to a specific sensor that can be used in a fall detector and other devices.

BACKGROUND TO THE INVENTION

Falling is a significant problem in the care of the elderly that can lead to morbidity and mortality. From a physical perspective, falls cause injuries, while from the mental perspective, falls cause fear-of-falling, which in turn leads to social isolation and depression.

Fall detection systems are being developed which can provide an automated and reliable means for detecting when a user has fallen. If a fall is detected, the system issues an alarm which summons help to the user. This assures the user that adequate measures will be taken in the event that a fall occurs.

Commonly, fall detectors are based on an accelerometer (usually a 3D accelerometer that measures acceleration in three dimensions) that is to be attached to the user's body. The fall detector processes the signals from the accelerometer to determine whether a fall has taken place. Unfortunately, however, as these fall detectors only include a single sensor, they often lack sensitivity and/or specificity.

Therefore, some fall detectors make use of further sensors, such as gyroscopes or air pressure sensors, to achieve high sensitivity and specificity.

However, each of these types of multiple sensor fall detectors have their own disadvantages. For example, gyroscopes provide highly reliable data, but they are unfeasible for a small body-worn portable device due to their size and energy consumption. Air pressure sensors can be used to provide altitude information (usually information on changes in altitude), but they only provide this altitude information at low sampling rates, making the reliable detection of falls challenging. Furthermore, it is difficult to mount air pressure sensors in fall detectors if the fall detector is to be water-resistant, which means that a special hydrophobic membrane and a dedicated pressure measurement chamber are required, as direct and sufficient air flow is required to the air pressure sensor.

Therefore, there is a need for an improved fall detector that overcomes the disadvantages with the conventional fall detectors described above.

SUMMARY OF THE INVENTION

According to a first aspect of the invention, there is provided a fall detector for detecting falls of a user or an object to which the fall detector is attached, characterized in that the fall detector comprises an air flow sensor for providing measurements indicative of vertical velocity and/or changes in altitude of the fall detector. Thus, the invention provides a fall detector that can estimate altitude changes and vertical velocity while avoiding the need for gyroscopes or air pressure sensors.

In preferred embodiments, the fall detector further comprises an accelerometer for measuring accelerations of the fall detector and a processor for processing the measurements from the air flow sensor and the accelerometer to determine whether a fall has occurred.

In a preferred embodiment, the processor is configured to estimate the orientation of the fall detector from the measurements from the accelerometer and to use the estimated orientation to generate a vertical velocity profile for the fall detector from the measurements from the air flow sensor.

In preferred embodiments, the air flow sensor is a thermal air flow sensor. Thermal air flow sensors reduce the power consumption of the fall detector, provide the ability to measure air flow direction through 360 degrees, are sensitive to low air flow rates and allow for a simple design of the housing of the device to ensure that it is water-resistant.

In preferred embodiments, the thermal air flow sensor comprises an electrically driven thermal element on a front side of the thermal air flow sensor arranged to face the channel, and a bond pad coupled electrically to the electrically driven thermal element, for making electrical contact off the thermal air flow sensor, the bond pad being arranged to face away from the front side to be accessible for contact from a backside of the thermal air flow sensor.

By having the bond pad accessible from the backside of the integrated circuit, facing away from the fluid channel, the space needed for the bond pad and any connections to it, need not extend beyond the electrically driven thermal element, e.g. the temperature sensing element and get in the way of the fluid channel. Hence the electrically driven thermal element, e.g. the temperature sensing element can be located closer to the fluid channel or in the fluid channel to enable better measurements.

Preferably, the thermal air flow sensor further comprises a conductive layer on the front side of the thermal air flow sensor, for electrical connection between the electrically driven thermal element and the bond pad, and the bond pad comprises a back side of the conductive layer. This has the advantage of providing an additional degree of freedom regarding the thermal conductivity of the thermal flow sensor device while providing a contact on the back side. For instance, the thickness of the conductive layer or the material comprised in the conductive layer may be employed as design variables.

Preferably, the thermal air flow sensor further comprises an insulating layer for electrically insulating the thermal air flow sensor from a fluid in the channel. Preferably, the insulating layer comprises poly-imide. Poly-imide has a thermal conductivity of about 0.15 W/(mK) and allows for disposition at a thickness of roughly 10 micron. As a result, thermal shunting is reduced. This advantageously increases sensitivity of the thermal flow sensor device. Furthermore the smaller thickness positively affects the response time associated with the thermal flow sensor device. In addition to that, poly-imide is easily applied by spin-coating methodologies, which methodologies advantageously circumvent the need for gluing.

Preferably, the thermal air flow sensor further comprises a substrate, the substrate being patterned to provide an aperture to expose the bond pad to enable contact with the bond pad through the aperture. This allows access to the bond pad while keeping a certain thickness of the substrate for mechanical strength and stability.

Preferably, the electrically driven thermal element comprises a heating element or a temperature sensor element on a front side of the thermal air flow sensor to face the channel. Location on the front side makes the temperature sensor more sensitive.

According to a second aspect of the invention, there is provided a method in a fall detector of detecting falls of a user or an object to which the fall detector is attached, the method comprising using an air flow sensor to provide measurements indicative of vertical velocity and/or changes in altitude of the fall detector.

Aspects also relate to sensor integrated circuits for sensing flow rate, to systems incorporating such integrated circuits, and to methods of manufacturing and operating such integrated circuits and such systems.

BRIEF DESCRIPTION OF THE DRAWINGS

The invention will now be described, by way of example only, with reference to the following drawings, in which.

DETAILED DESCRIPTION OF THE PREFERRED EMBODIMENTS

Although the invention will be described herein with reference to a fall detector that is to be worn by a person and that detects falls by that person, it will be appreciated that the fall detector and method of detecting falls according to the invention can be put to alternative uses, such as detecting falls in objects, for example hard disks or other sensitive electronic equipment.

The invention provides a fall detector that comprises an air flow sensor for providing measurements indicative of vertical velocity and/or changes in altitude of the fall detector. In preferred embodiments, the fall detector comprises a further sensor or sensors, for example a sensor for measuring, or providing measurements indicative of, acceleration (such as an accelerometer). In these embodiments, the measurements from the air flow sensor are used to determine altitude changes and/or the vertical velocity of the fall detector, and these are processed in combination with the acceleration measurements to determine whether a fall has occurred.

Figure 1:
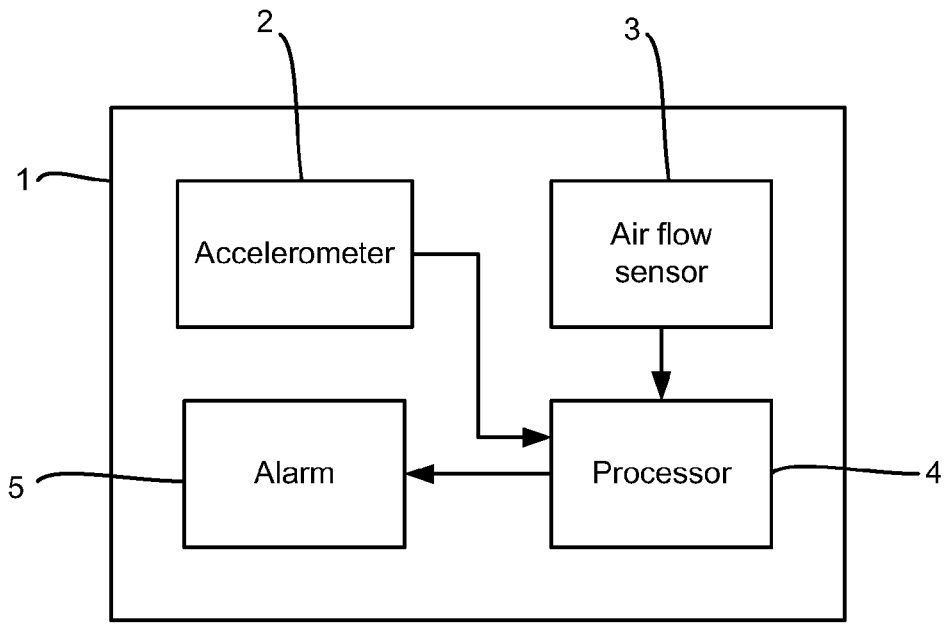
FIG. 1 is an illustration of a fall detector in accordance with the invention.

FIG. 1 illustrates a fall detector 1 in accordance with the invention. The fall detector 1 can be suitable for a user to wear on the upper part of their body, for example around their waist, on their chest, at their wrist, or as a pendant around their neck. The fall detector 1 comprises an accelerometer 2 that measures the acceleration experienced by the fall detector 1, an air flow sensor 3 that provides measurements of the speed and direction of air flow around the fall detector 1, a processor 3 that receives the measurements from the accelerometer 2 and air flow sensor 3 and that processes the measurements to determine whether a fall has occurred.

The fall detector 1 further comprises an alarm 5 that can be triggered by the processor 4 if it is determined that a fall has occurred. In alternative embodiments, the fall detector 1 can also or alternatively include means for wirelessly transmitting an alarm signal to a call-centre or other remote assistance unit, unless the user gets up after a detected fall quickly.

Figure 2:
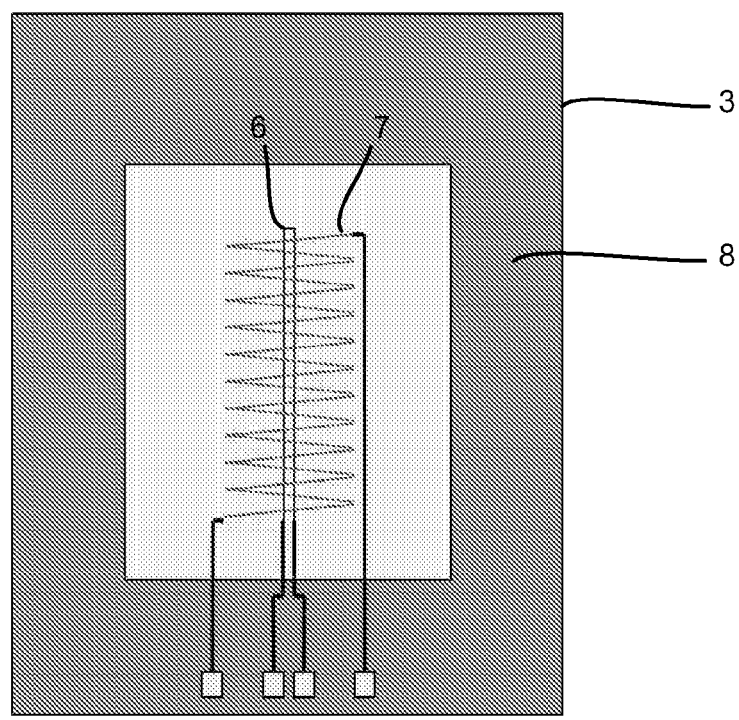
FIG. 2 is an illustration of an air flow sensor for use in the fall detector according to the invention.

The air flow sensor 3 can comprise any type of air flow sensor, for example ultrasonic, differential pressure or impellor-based sensors, but, in a preferred embodiment of the invention, the air flow sensor 3 comprises a thermal air flow sensor, a simplified version of which is shown in FIG. 2. A thermal air flow sensor is preferred as it has low power consumption (and so can be used in a portable device with a battery), the possibility of measuring air flow direction through 360 degrees, and is sensitive to low air flow rates. Furthermore, the thermal air flow sensor is able to shield the sensor portion from the airflow, which allows a simple design of the housing of the device to ensure that it is water-resistant.

An exemplary thermal flow sensor that can be used in the fall detector 1 according to the invention (and a method of manufacturing such a thermal flow sensor) is described in detail in the "Thermal Flow Sensor" section below.

Referring to FIG. 2, the thermal air flow sensor 3 comprises a heater element 6 (which corresponds to a resistance that is kept at constant power or constant temperature) and one or more temperature sensing elements 7 (thermocouples or resistors) that measure temperature differences over the surface of the sensing elements 7. Preferably, the temperature sensing element 7 comprises a thermopile (which is a plurality of thermocouples connected in series) as it directly measures a temperature difference with a high sensitivity and zero offset. The thermal air flow sensor 3 can be mounted onto a printed circuit board or other structure in the fall detector 1 as described in the "Thermal Flow Sensor" section below so that the fall detector 1 is water-resistant.

At zero flow, heat transfer from the thermopile 7 to the fluid 8 in the sensor 3 occurs through conduction, which leads to a symmetric temperature distribution over the surface of the thermopile 7. If a certain fluid flow exists, heat is transferred through convection.

Convective heat transfer consists of two mechanisms; energy is not only transferred by conduction, but also by the bulk motion of the fluid 8 in the presence of a temperature gradient (advection). Convective heat transfer leads to an asymmetric temperature distribution; at the upstream part the thermopile 7 is cooled more than at the downstream part, since hot fluid 8 is advected in the downstream direction, leading to a temperature difference over the surface of the thermopile 7.

Preferably, the thermal air flow sensor 3 is manufactured using an integrated circuit (IC) process for its high reproducibility and the possibility to downscale the footprint of the sensor. For example, the thermal air flow sensor 3 can be manufactured according to the processes described in the "Thermal Flow Sensor" section below. A further advantage of fabricating the thermal air flow sensor 3 in an IC process is the possibility to integrate electronics such as amplifiers, A/D converters and microcontrollers onto the chip to further reduce the dimensions, cost and energy consumption of the fall detector 1.

Figure 3:
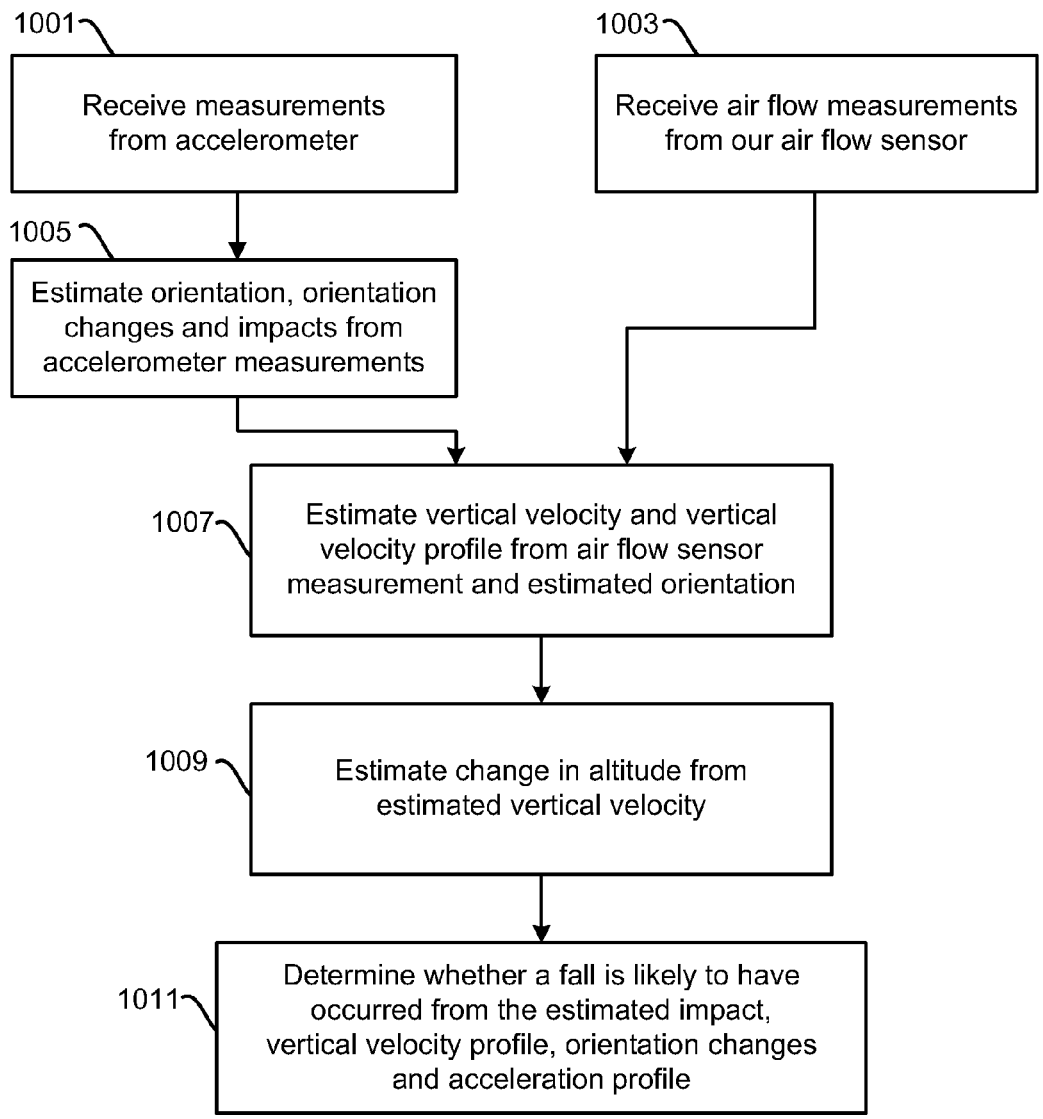
FIG. 3 is a flow chart illustrating a method of detecting falls in accordance with the invention.

A method of detecting falls in accordance with the invention (which corresponds to the method executed by the processor 4 in the fall detector 1) will now be described with reference to FIG. 3.

In step 1001, the processor 4 receives measurements from the accelerometer 2 and in step 1003, the processor 4 receives measurements of air flow from the air flow sensor 3. These two types of measurements are received substantially in parallel, as shown in FIG. 3.

In step 1005, the processor 4 estimates the orientation of the fall detector 1, any change in the orientation of the fall detector 1 and whether any impacts have occurred from the measurements from the accelerometer 2.

Processing techniques for estimating the orientation of an object from accelerometer measurements are known in the art and will not be described further herein.

In step 1007, the processor 4 uses the orientation of the fall detector 1 estimated in step 1005 and the measurements from the air flow sensor 3 to estimate the vertical velocity of the fall detector 1 and a vertical velocity profile (i.e. a profile indicating how the vertical velocity of the fall detector 1 changes over time).

In particular, the processor 4 uses the estimated orientation to identify the component of the air flow measurements that correspond to the vertical direction.

Typically, the air flow sensor 3 has an air guiding channel and the processor 4 can use the estimated orientation to estimate the orientation of the air guiding channel and therefore determine whether there is air flow in the vertical direction.

In step 1009, the processor 4 uses the estimated vertical velocity to estimate the change in altitude of the fall detector 1 over time (for example by integrating the vertical velocity profile over a particular time period).

In step 1011, the processor 4 determines whether a fall has or is likely to have occurred from the vertical velocity profile, an acceleration profile (which will indicate the timing and magnitude of any impacts and the presence of any 'quiet' periods after impacts where the acceleration is in a steady state—only gravity is present), the changes in orientation of the fall detector 1 and the estimated altitude change. Those skilled in the art will be aware of a number of algorithms that the processor 4 can use to process this information to determine if a fall has taken place.

There is therefore provided a fall detector and method of detecting falls that overcomes the disadvantages of conventional fall detectors and fall detection methods, and in particular embodiments results in a fall detector with (i) low power consumption, (ii) the ability to measure air flow direction through 360 degrees, (iii) sensitivity to low air flow rates and (iv) a simple design of the housing of the device to ensure that it is water-resistant.

Thermal Flow Sensor

Aspects of the invention relating to thermal flow sensor integrated circuits for sensing flow in a channel based on temperature measurements described below comprise an integrated circuit having a temperature sensing element on a front side of the integrated circuit to face the fluid channel, and a bond pad coupled electrically to the temperature sensing element, for making electrical contact off the integrated circuit, the bond pad being arranged to face away from the front side to be accessible for contact from a backside of the integrated circuit.

In some of the embodiments of the thermal flow sensor, an Integrated Circuit (IC) processed thermal flow sensor is shown with bond pads fabricated at the backside of the sensor to enable easy mounting, and a fast and sensitive sensor response. Since the bond pads are fabricated in a post-processing step, the steps described can be compatible with mainstream IC processes such as CMOS processing, especially standard CMOS processing, thus enabling the integration of on-integrated circuit driving electronics. In another embodiment of the thermal flow sensor, the sensor can be mounted on a printed circuit board (PCB) in a pick-and-place procedure to enable high volume, low cost production.

In some embodiments of the thermal flow sensor, there is a metal layer on the front side of the integrated circuit, for electrical connection between the sensing element and the bond pad, and the bond pad comprises the back side of the metal layer. This enables the bond pad to be relatively close to the sensing element to keep the structure simple and compact. An example is shown in the first embodiment of the thermal flow sensor described below.

In some embodiments of the thermal flow sensor, the integrated circuit comprises a substrate and the substrate is patterned to provide an aperture to expose the bond pad to enable contact to the bond pad through the aperture. This can help protect the contact and provide a compact structure.

In some embodiments of the thermal flow sensor the integrated circuit comprises a substrate and the substrate is patterned to form one or more pillars, and the bond pad is located on a back side of the substrate on one of the pillars. The pillars can provide support for the bond pad, and maintain isolation from other circuitry. An example is shown in the second embodiment of the thermal flow sensor described below.

In some embodiments of the thermal flow sensor the integrated circuit comprises a heating element on a front side of the integrated circuit to face the fluid channel. This enables a more integrated solution, though in alternative embodiments of the thermal flow sensor, the heating can be provided by a heater external to the integrated circuit. The external heater should be provided so that the fluid is heated sufficiently closely to the temperature sensor.

In some embodiments of the thermal flow sensor the integrated circuit comprises a silicon on insulator integrated circuit. This helps enable other circuit elements to be integrated. The third embodiment of the thermal flow sensor described below discloses this arrangement.

In some embodiments of the thermal flow sensor there is an assembly comprising a printed circuit board and the integrated circuit of any embodiment, mounted on the printed circuit board, with the bond pad coupled to a corresponding contact on the printed circuit board. This enables other circuit elements to be mounted on the board, as an alternative to having them integrated on the same integrated circuit, which could be less expensive or easier to manufacture. It also allows additional components to be included with the integrated circuit. An example is shown in the fourth embodiment of the thermal flow sensor described below.

In some embodiments, there is a system having a fluid channel for the fluid flow, the channel having a wall having a recess, and in the recess is the integrated circuit or the assembly, with the sensing element facing the channel.

The aspects relating to the thermal flow sensor also provide a method of manufacture of a thermal flow sensor integrated circuit for sensing flow in a fluid channel based on temperature measurements, which can involve the steps of forming an electrically driven thermal element such as a temperature sensing element on a front side of the integrated circuit arranged to face the fluid channel, and forming a bond pad coupled electrically to the electrically driven thermal element such as the temperature sensing element, for making electrical contact off the integrated circuit, the bond pad being arranged to face away from the fluid channel.

The method of manufacturing a thermal flow sensor can involve the step of forming the bond pad on a backside of a metal layer, or patterning a substrate to form an aperture, and forming the bond pad in the aperture, or patterning a substrate to form a pillar and forming the bond pad on the pillar.

In summary, the embodiments of the thermal flow sensor described involve an IC processed thermal flow sensor with bond pads fabricated at the backside of the sensor. As the bond pads can be fabricated in a post-processing step, at least some embodiments of the thermal flow sensor are compatible with mainstream IC processes such as CMOS processing, especially standard CMOS processing, thus enabling the integration of, for example, on-integrated circuit driving electronics. In another embodiment of the thermal flow sensor a method to mount the sensor on a PCB in a pick-and-place procedure is shown to enable high volume, low cost production.

A thermal flow sensor typically comprises one or more heating elements and/or one or more temperature sensing elements such as resistors, transistors or thermocouples. The heating element (on integrated circuit or elsewhere) heats up the part of the fluid that is located close to the sensor. The fluid flow induces a decrease in the heater temperature and a shift in the temperature profile of the integrated circuit, which can be measured with the temperature sensing elements. Both the heater temperature as well as the shift in temperature profile can be used as a measure for the flow rate. An additional benefit of the temperature profile measurement is the ability to determine flow direction.

In embodiments of the thermal flow sensor, the term "substrate" may include any underlying material or materials that may be used, or upon which a device, a circuit or an epitaxial layer may be formed. In other alternative embodiments of the thermal flow sensor, this "substrate" may include a semiconductor substrate such as e.g. silicon, doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or a $Si_3N_4$ layer in addition to a semiconductor substrate portion. Thus, the term substrate also includes silicon-on-glass, silicon-on sapphire substrates. The term "substrate" is thus used to define generally the elements for layers that underlie a layer or portions of interest.

A first embodiment of the thermal flow sensor is an integrated circuit manufactured as shown in FIGS. 4 to 16, having a bond pad accessible through an aperture in the substrate.

Figure 4:
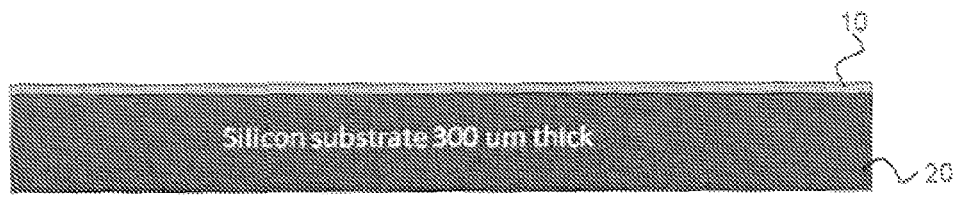
FIGS. 4 to 16 show steps in a method of manufacturing an integrated circuit, having a bond pad accessible through an aperture in the substrate.

FIG. 4 shows the starting material, in this case a semiconductor substrate such as a semiconductor wafer of which a 300 micron thick silicon substrate 20 with an insulating layer on top such as an oxide layer, e.g. a 0.5 micron thermal oxide layer 10 on top is an example. Other insulating layer thicknesses or insulating layer materials could be used such as silicon nitride. The heating elements and temperature sensing elements can be processed using standard deposition and lithography techniques (shown in FIGS. 5 to 10).

Figure 5:
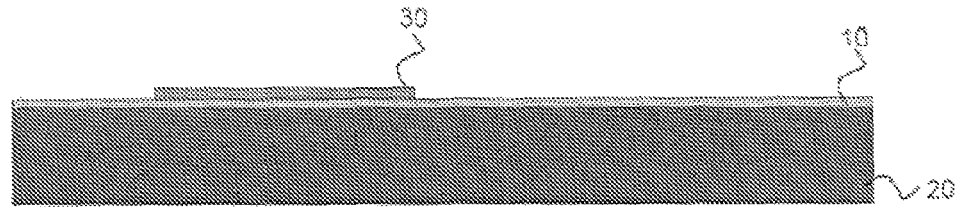

FIG. 5 shows the formation of an electrically driven thermal element such as a thermal resistor, e.g. deposition and patterning of 0.3 micron in-situ doped (n++) polysilicon layer 30 using a first mask: MASK 1:PS. Polysilicon layer 30 can be formed into one or more heating elements and/or one or more temperature sensing elements such as resistors, transistors or thermocouples. The heating element can be located separately and the polysilicon layer is only used a temperature sensing element. Where a heating element is provided this heats up the part of the fluid that is located close to the sensor. The fluid flow induces a decrease in the heater temperature, which can be measured with a temperature sensing element. Both the heater temperature as well as the shift in temperature of the temperature sensor can be used as a measure for the flow rate.

Figure 6:
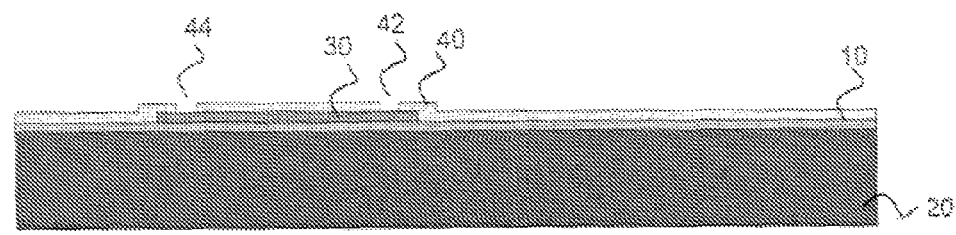
Figure 7:
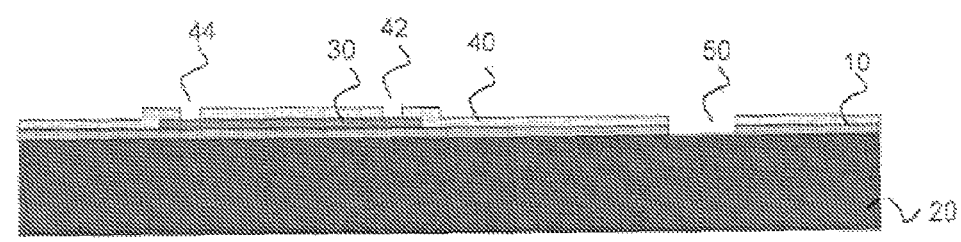
Figure 8:
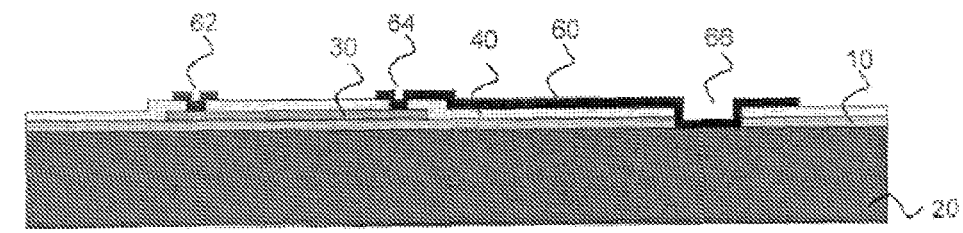

FIG. 6 shows formation of a pre-metal dielectric layer such as a 0.2 micron TEOS layer 40 and opening of first contact holes 42, 44 over the thermal element, e.g. polysilicon layer 30. This uses a second mask: MASK 2: CO. FIG. 7 shows the opening of second contact holes 50 to the substrate for bondpads. This can use a third mask: MASK 3: CB. In FIG. 8 is shown formation of a conductive layer that can be a metallization layer such as a metal stack, e.g. a 20 nm Ti+0.5 Aluminum metallization layer 60 to make electrical contact between the elements especially contacts 62, 64 to the thermal element made of polysilicon 30 through the first contact holes 42, 44 and the contact 66 to the bond pad hole or second contact hole 50. This can use a fourth mask: MASK 4:IN. The contacts 62, 64, 66 allow the electrical connections to drive the thermal element and to operate the sensor.

Figure 9:
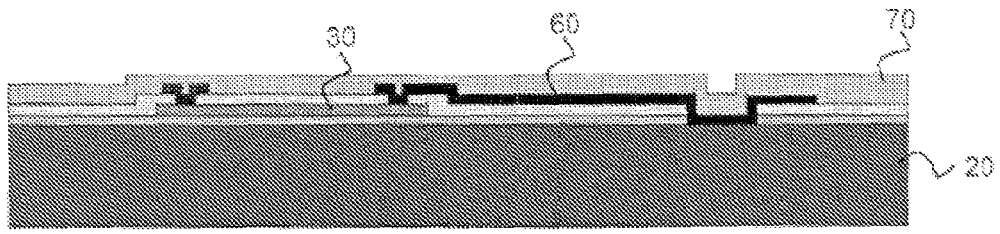
Figure 10:
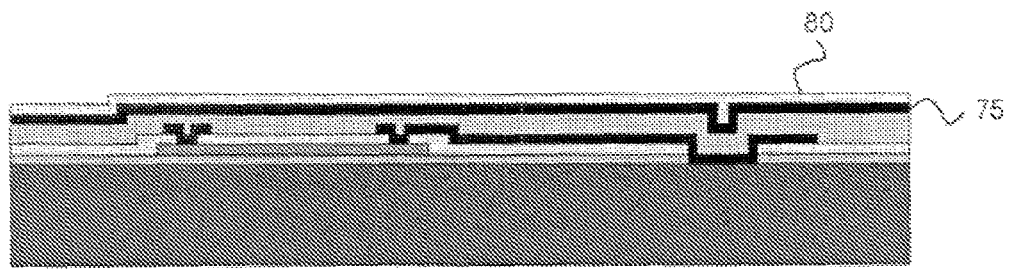

FIG. 9 shows forming a passivation layer and a scratch protection layer over the complete device such as forming a 0.5 micron PECVD nitride and 0.5 micron oxide layer 70 for passivation and scratch protection. The part of the sensor which will be closest to the fluid channel is above the polysilicon layer 30 so that further layers may be deposited to provide thermal conductance and to improve adhesion, e.g. FIG. 10 shows forming a metal layer such as a 0.05-1 micron aluminum layer 75 to tune thermal conductivity and an insulating layer such as a 0.5 micron oxide layer 80 for adhesion. To obtain optimal response time and sensitivity the average thermal conductance of the stack can be tuned by adapting the thickness of an additional (un-patterned) metallization layer.

Figure 11:
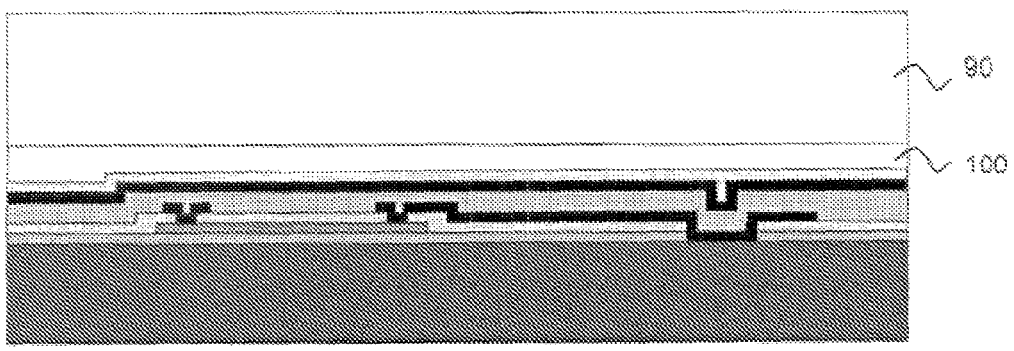
Figure 12:
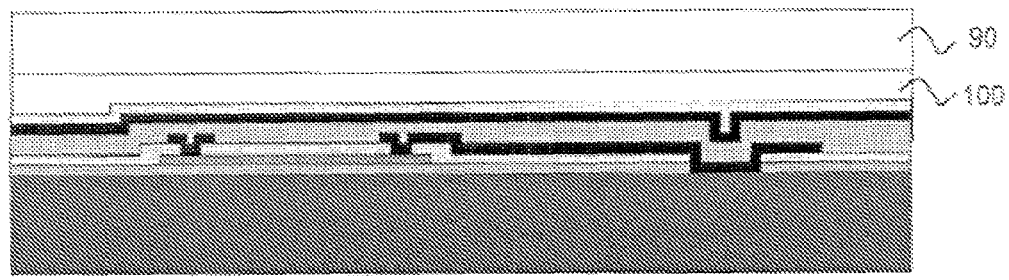

FIG. 11 shows a bonding process to a chemically resistant smooth and flat surface layer. For example, glue 100 is applied followed by an insulating substrate 90. The insulating substrate 90 may be manufactured from glass, which has a thermal conductivity of about 1 W/(mK). When manufactured from glass; the insulating substrate will typically have a thickness of about 400 micron. This can be implemented by placing the semiconductor wafer top down on the insulating substrate 90. Then the insulating substrate 90 is optionally thinned, e.g. by (DISCO-) grinding to a thickness of 50-100 micron followed by an optional polishing step to ensure a smooth sensor surface as shown in FIG. 12. Alternatively, the insulating substrate 90 is manufactured from poly-imide which has a thermal conductivity of about 0.15 W/(mK) and a thickness of roughly 10 micron. As a result, thermal shunting of the area in which the sensor is to be situated is reduced. This advantageously increases sensitivity of the sensor. Furthermore the smaller thickness positively affects the sensor's response time. In addition to that, poly-imide is easily applied on the semiconductor wafer, e.g. by spin-coating methodologies, which methodologies advantageously circumvents the need for gluing the insulating substrate 90.

Figure 13:
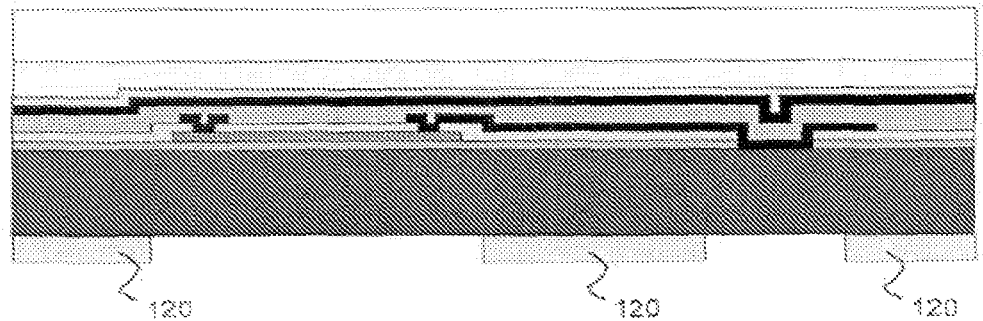

FIG. 13 shows forming a backside mask 120, e.g. a resist layer, for anisotropic etching such as deep RIE etching using a fifth mask: MASK 5:CAV.

Figure 14:
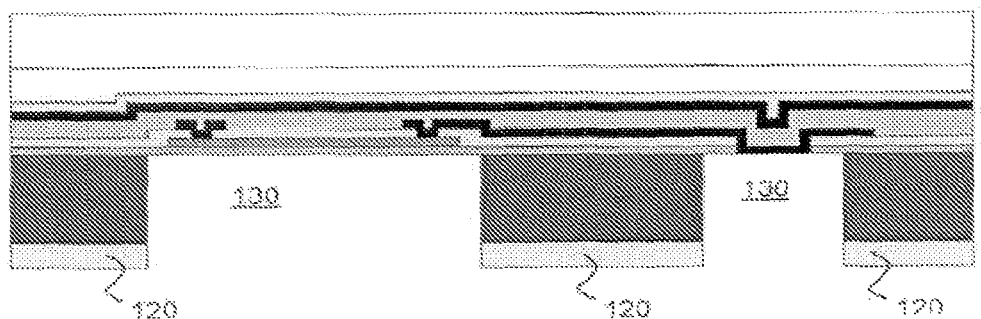

FIG. 14 shows forming the apertures 130 in the semiconductor substrate to open the bondpads by locally removing the semiconductor material, e.g. silicon. This can involve anisotropic etching such as a deep RIE etching (Bosch process) stopping on the insulating layer, e.g. oxide 10 and the conductive layer 60, e.g. metal, e.g. aluminum bondpads. Note that the aluminum bondpads are located directly on the silicon substrate so that removing the substrate opens the bond pad. Optionally, the silicon underneath the sensing area can be removed to increase the sensor sensitivity. The remaining silicon provides mechanical strength and functions as a heat sink. Now the sensor can be contacted e.g. using wirebonding.

Figure 15:
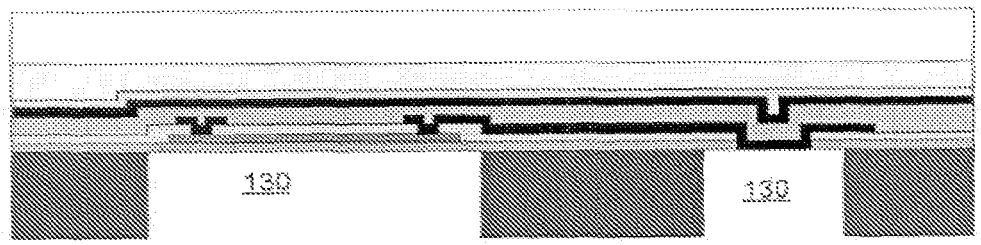
Figure 16:
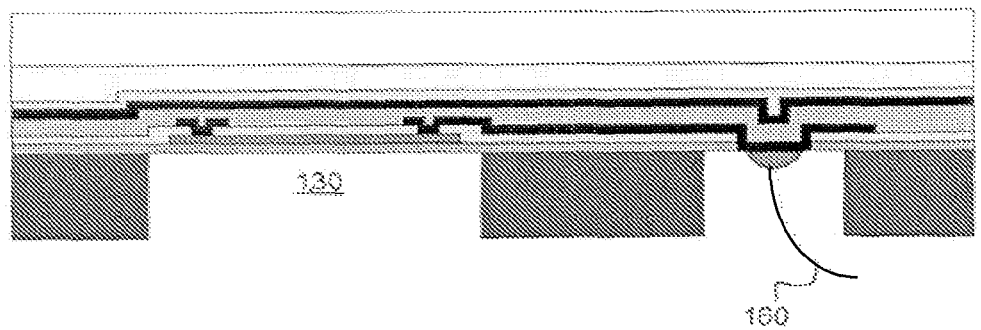

FIG. 15 shows removing the backside mask, e.g. resist layer 120. FIG. 16 shows a final step of dicing and providing a wirebond 160 to external circuitry such as a PCB or flexfoil.

A second embodiment of the thermal flow sensor involves fabricating electrically isolated semiconductor, e.g. silicon, 'pillars' to move the electrical connection of the sensor to the backplane of the stack. A starting material is for example a semiconductor wafer, e.g. a highly doped low resistive substrate with an insulating layer on top such as a thermal oxide layer on top. The heating elements and/or temperature sensing elements are processed using standard deposition and lithography techniques and are as shown in FIGS. 5 to 10 described in relation to the first embodiment of the thermal flow sensor, i.e. from the polysilicon layer 30. To obtain optimal response time and sensitivity the average thermal conductance of the stack can be tuned by adapting the thickness of an additional metallization layer as shown in FIG. 10.

The wafer is bonded e.g. by gluing top down to a glass substrate as shown in FIG. 11, and the glass substrate is optionally thinned by (DISCO-) grinding to a thickness of 50-100 micron followed by a polish step to ensure a smooth sensor surface as shown in FIG. 12. In place of the method steps described with respect to FIGS. 13 to 16 of the first embodiment of the thermal flow sensor, the second embodiment of the thermal flow sensor has steps shown in FIGS. 17 to 22.

Figure 17:
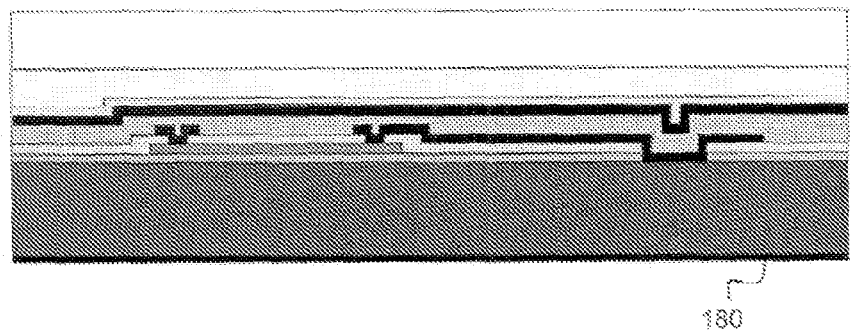
FIGS. 17 to 24 show steps in an alternative method of manufacturing an integrated circuit, having the bond pad on a pillar on a backside of the substrate.
Figure 18:
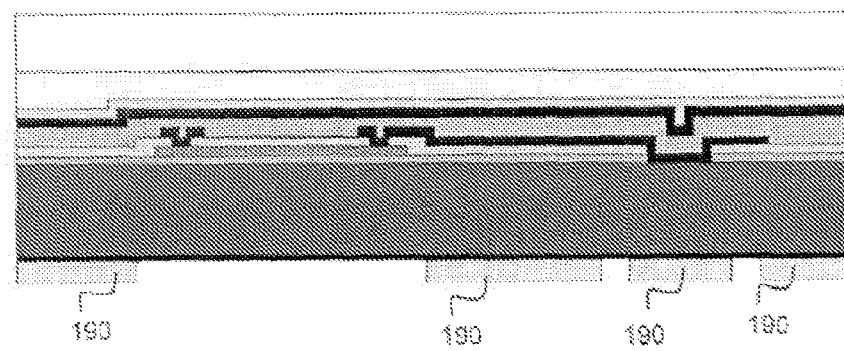
Figure 19:
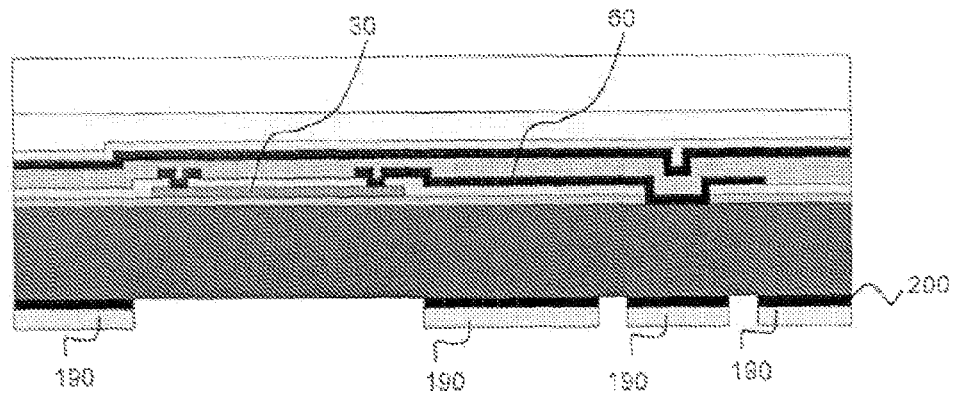

FIG. 17 shows the deposition of a metal layer such as a 0.5 micron aluminum layer 180 on a backside of the wafer for example by sputtering. FIG. 18 shows a backside mask for anisotropic etching, e.g. deep RIE etching: MASK 5:CAV. This can be a resist layer 190. This is used to pattern the metal layer, e.g. aluminum layer 180 to define the bond pads 200 as shown in FIG. 19.

Figure 20:
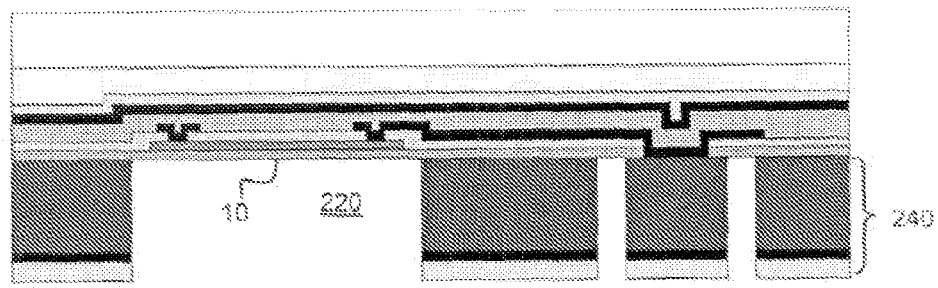

FIG. 20 shows anisotropic etching, e.g. deep RIE etching (Bosch process) stopping on the oxide layer 10 (and any aluminum layer 60). This enables the silicon 220 underneath the sensing area to be removed to increase the sensor sensitivity, and the silicon around the bondpads is removed to form electrically isolated silicon 'pillars' 240 providing an electrical connection between the sensor and the bondpads. The remaining silicon provides mechanical strength and functions as a heat sink for the sensor. Now the sensor can be contacted e.g. using wirebonding.

Figure 21:
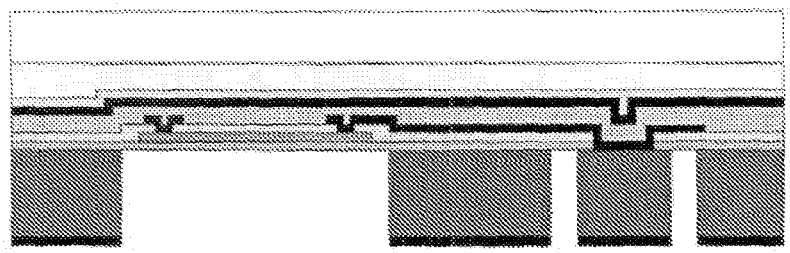

FIG. 21 shows removing the resist layer.

Figure 22:
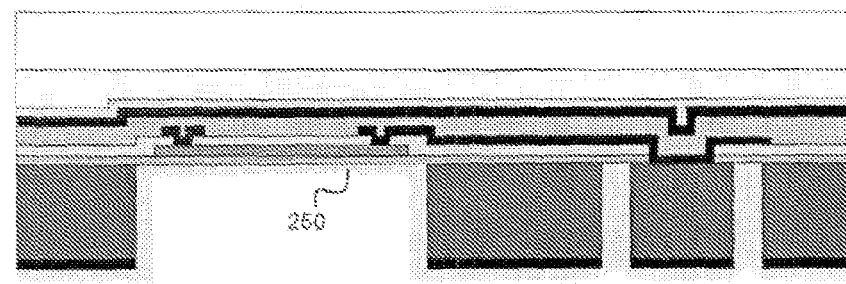

FIG. 22 depicts providing a coating 250 of electrical resistive material at the backside of the stack. Herein the trenches between the pillars 240 are filled with the coating 250. Also the remaining silicon substrate is provided with the coating 250 of electrical resistive material. Preferably, the coating 250 comprises parylene. The coating 250 has a thickness such that trenches between the pillars are completely filled, i.e. the coating 250 has a thickness that equals roughly half the width of the trenches between the pillars 240.

Figure 23:
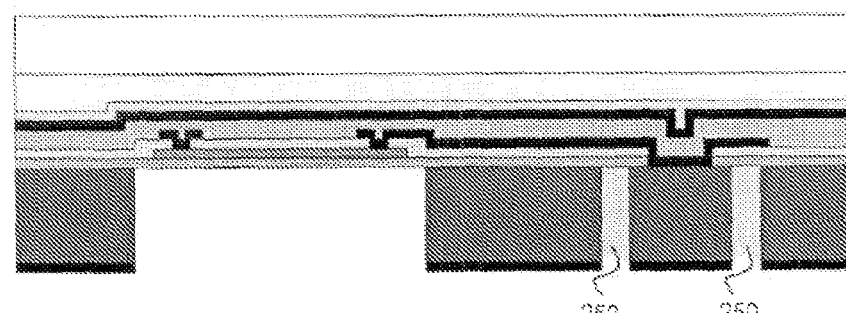

FIG. 23 displays removing the coating 250 by way of applying an oxygen plasma to it until all coating 250 is removed from the oxide layer 10 and the pillar's top surfaces. Only a small fraction will be removed of the coating 250 deposited in the trenches between the pillars 240, this fraction will have a thickness that is more or less equal to the original thickness of the coating 250.

Figure 24:
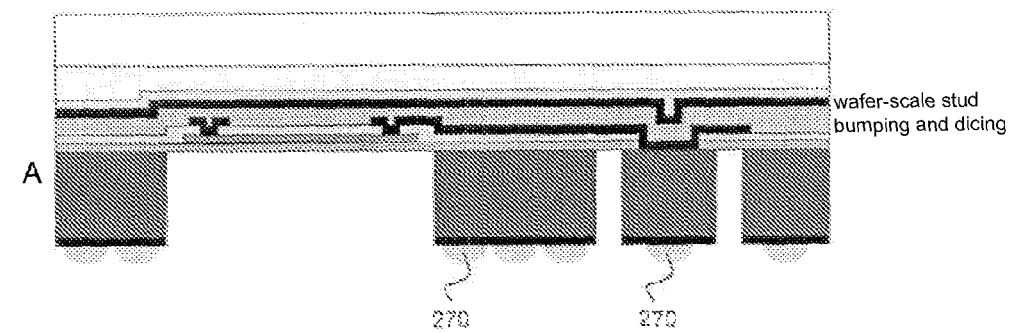

FIG. 24 shows wafer-scale processing to form stud bumps 270. This can be followed by dicing of the wafer to provide individual integrated circuits.

A third embodiment of the thermal flow sensor involves fabricating the sensors of embodiments 1 and 2 using the same steps as described above but the starting material is an SOI (silicon-on-insulator) wafer having a mono-crystalline upper layer above an insulating layer. In this embodiment of the thermal flow sensor, driving electronics such as A/D converters etc. can be processed in the mono-crystalline silicon layer of the SOI. Also the temperature sensing elements can be processed in the mono-crystalline silicon instead of using a separate polysilicon layer 30.

Figure 25:
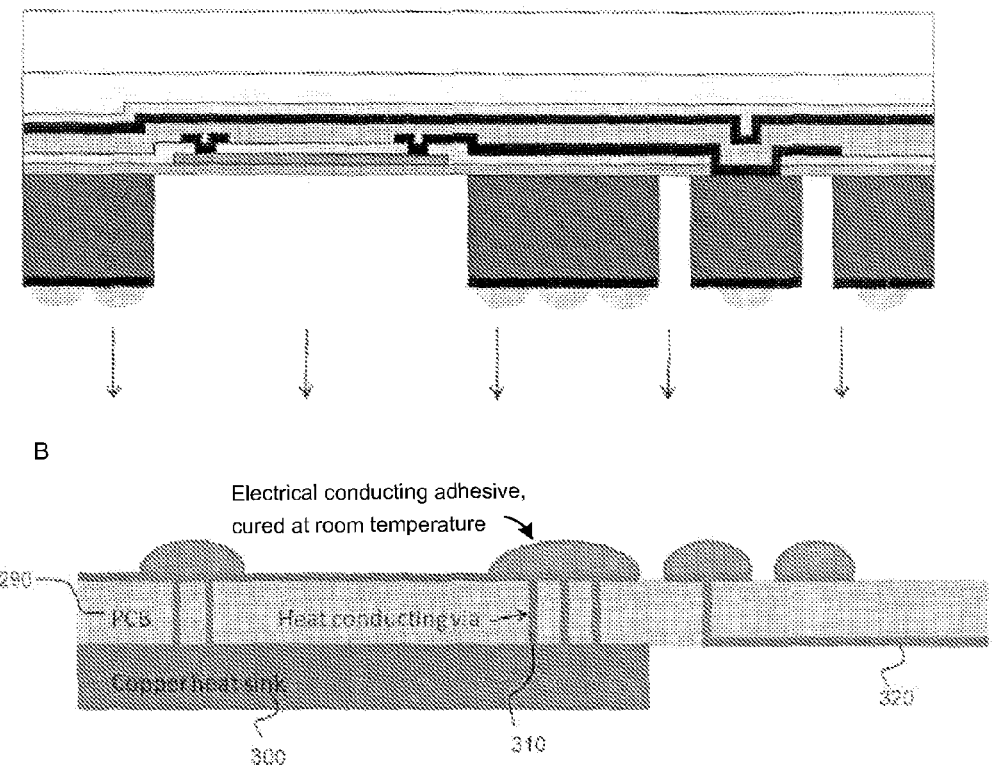
FIG. 25 shows forming an assembly by mounting the integrated circuit on a PCB.
Figure 26:
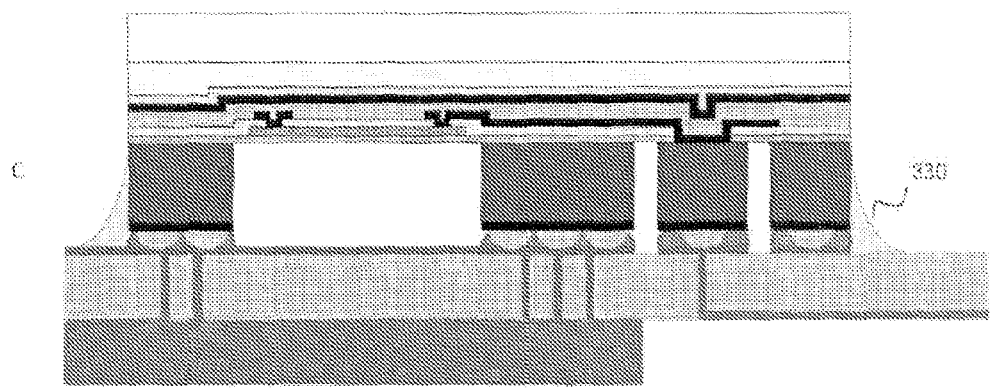
FIG. 26 shows applying sealant to the assembly.

In a fourth embodiment of the thermal flow sensor a method to mount the sensor stack as described in any of the embodiments of the thermal flow sensor is presented. As an example the sensor device as in the second embodiment of the thermal flow sensor is mounted directly on a PCB as shown in FIGS. 25 and 26. Stud bumps are applied on the bond pads to provide a good electrical connection to the PCB 290. Additionally, stud bumps are applied underneath the silicon heat sink to provide a good thermal connection to the PCB. Electrical conductive adhesive 280 is applied on the PCB. The adhesive should be chosen to reduce the mismatch of the thermal expansion coefficients of the silicon and the PCB. Preferably a conductive epoxy that is cured at room temperature is used to prevent introduction of stress in the sensor due to a mismatch of the thermal expansion coefficients of the silicon and the PCB. To avoid penetration of water (vapor) and dirt into the gap between the sensor and the PCB an adhesive 330 is applied to seal the sensor. A heat sink 300 can be mounted at the backside of the PCB and connected with the silicon heat sink by thermally conductive vias 310 through the PCB. Electrical connections 320 are shown for coupling the bond pads of the sensor to other components on the PCB. These connections can include conventional vias and printed copper lines.

Figure 27:
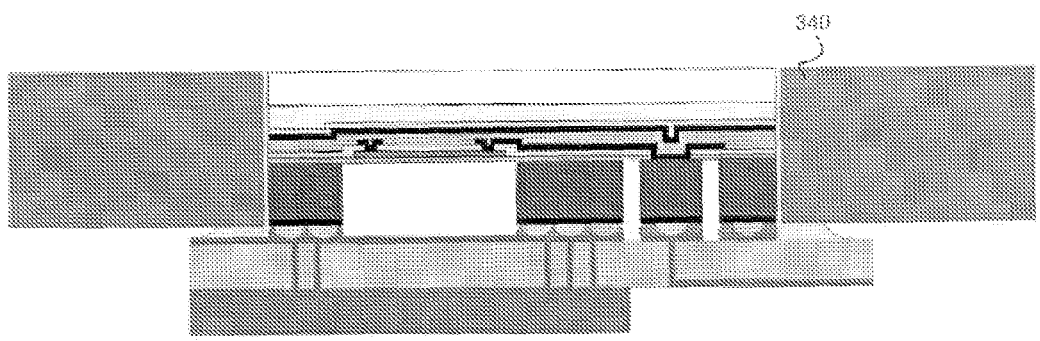
FIGS. 27 and 28 show the assembly mounted in a channel wall.
Figure 28:
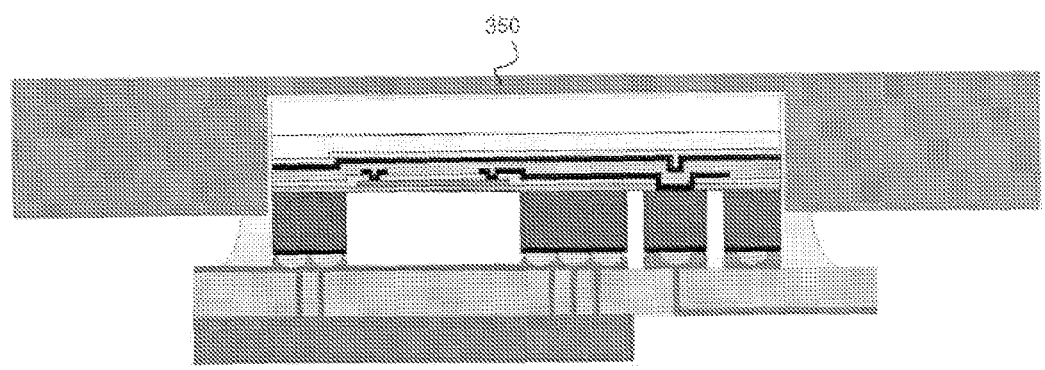

FIG. 27 shows the mounting of the assembly having the flow sensor according to any of the embodiments of the thermal flow sensor in a recess in the form of a prefabricated window in the flow channel wall 340. In this view the flow channel is above the sensor. FIG. 28 shows the mounting of the flow sensor behind an alternative type of recess in the form of a locally thinned part 350 of the flow channel wall. This thinned part can provide a barrier to reduce a risk of leakage or contamination of the fluid, and avoid a need to provide a good seal around the edges of the sensor integrated circuit.

The sensors, assemblies and fabrication methods are not restricted to be applied in fall detectors. For example, they could be applied in nebulizer systems or other medical applications where sterility is required such as in IV infusion drug delivery. Also they can be applied in applications other than medical fields, e.g. for use in environments with aggressive fluids.

In embodiments of thermal flow sensors, the sensor is located on top or in the upper layer of a silicon substrate. Conventionally both the sensor area and the bond pads to connect the sensor with e.g. driving electronics located at the front side of the silicon stack. In such conventional devices the sensor area and the bond pads are located in a same plane, so that when embedding the thermal flow sensor in the wall of a tubing, it is necessary to apply a thick layer between the sensor and the fluid flowing though the tubing in order to provide room and to protect and guide the connecting wires to a PCB or lead frame. The embodiments of the thermal flow sensor described can address this problem which can affect the performance of the sensor in terms of sensitivity and response time. Decreasing the distance between the temperature sensing elements comprised in the thermal sensor and the fluid flowing through the fluid channel by the embodiments described above can improve response time and sensitivity of the sensor.

In summary therefore, this aspect provides alternative sensors and sensor integrated circuits for sensing flow rate, to systems incorporating such sensors or sensor integrated circuits, and to methods of manufacturing and operating such sensors or sensor integrated circuits and such systems. According to a first aspect, a thermal flow sensor device is provided. This device comprises a thermal flow sensor integrated circuit or Integrated Circuit (IC) thermal flow sensor including an integrated circuit for sensing flow in a fluid channel based on temperature measurements, the integrated circuit having an electrically driven thermal element, e.g. a temperature sensing element on a front side of the integrated circuit to face the fluid channel, and a bond pad coupled electrically to the electrically driven thermal element, e.g. the temperature sensing element, for making electrical contact off the integrated circuit, the bond pad being arranged to face away from the front side to be accessible for contact from a backside of the integrated circuit.

By having the bond pad accessible from the backside of the integrated circuit, facing away from the fluid channel, the space needed for the bond pad and any connections to it, need not extend beyond the electrically driven thermal element, e.g. the temperature sensing element and get in the way of the fluid channel. Hence the electrically driven thermal element, e.g. the temperature sensing element can be located closer to the fluid channel or in the fluid channel to enable better measurements.

Accurate flow rate sensing is needed in many applications. One such application is in fall detection, and another is in the monitoring and control of intravenous delivery of a medication. Another such application is in nebulizer systems. Nebulizer systems are used to deliver drugs in the form of aerosols to patients with respiratory diseases. To enable accurate medication or aerosol delivery, the exact time period for the medication or aerosol release is determined based on flow sensor data. Such a flow sensor should be fast and sensitive to resolve velocity fluctuations, for instance around the turning point of inhalation to exhalation and vice versa.

Medical devices such as nebulizers may require sterilization in an autoclave, or with the use of mechanical or chemical methods. The ability to measure flow through the wall of a fluid channel makes it possible to mount the flow sensor and the electronics in a hermetically sealed part of the device, separated from the sterile environment. However, for good sensor performance in terms of sensitivity and response time the sensor should be mounted close to the fluid.

Thermal flow sensor integrated circuits are fabricated, using IC processing techniques, on top or in the upper layer of a silicon substrate. Consequently, both the sensor area and the bond pads to contact the sensor, are located at the front side of the silicon stack. Since the sensor area and the bond pads are located in the same plane it is necessary to apply a thick layer between the sensor and the fluid to protect and guide the connecting wires to a PCB or lead frame. The performance of the sensor in terms of sensitivity and response time decreases with the distance between the flow and the fluid.

A conductive layer can be provided on the front side of the thermal flow sensor device, for electrical connection between the electrically driven thermal element and the bond pad, and the bond pad comprises a back side of the conductive layer. This has the advantage of providing an additional degree of freedom regarding the thermal conductivity of the thermal flow sensor device while providing a contact on the back side. For instance, the thickness of the conductive layer or the material comprised in the conductive layer may be employed as design variables.

The thermal flow sensor device may comprise an insulating layer for electrically insulating it from a fluid in the channel. Preferably, the insulating layer comprises poly-imide. Poly-imide has a thermal conductivity of about 0.15 W/(mK) and allows for disposition at a thickness of roughly 10 micron. As a result, thermal shunting is reduced. This advantageously increases sensitivity of the thermal flow sensor device. Furthermore the smaller thickness positively affects the response time associated with the thermal flow sensor device. In addition to that, poly-imide is easily applied by spin-coating methodologies, which methodologies advantageously circumvent the need for gluing.

The device can include a substrate, such as a semiconductor substrate. The substrate can be patterned to provide an aperture to expose the bond pad to enable contact with the bond pad through the aperture. This allows access to the bond pad while keeping a certain thickness of the substrate for mechanical strength and stability.

The substrate may also be patterned to form one or more pillars, and the bond pad can be located on a back side of the substrate on one of the pillars.

The pillars may be provided with a coating of electrical resistive material in order to increase the mechanical support of the pillars. As a result, a cross-sectional size of the pillars may be decreased while materializing sufficient mechanical strength. A reduction of the pillars' cross-sectional size decreases the size of the IC, and therefore advantageously decreases the costs of the ID. Preferably, the electrical resistive material comprises parylene since the latter material has very good step-coverage properties. Because of said excellent step-coverage properties, parylene will cover sidewalls of the pillars with almost the same rate as the horizontal surface of the substrate. An example of a suitable parylene is poly-xylylene.

The electrically driven thermal element can comprise a heating element or a temperature sensor element on a front side of the thermal flow sensor device to face the channel. Location on the front side makes the temperature sensor more sensitive.

The device can be formed as an integrated circuit. This makes a compact device that can be easily included within other equipment. The IC can be a silicon on insulator integrated circuit.

Aspects also provide an assembly comprising a printed circuit board and the thermal flow sensor device described above mounted on the printed circuit board, with the bond pad coupled to a corresponding contact on the printed circuit board.

Aspects also provide a system having a channel, the channel having a wall, the wall having a recess, and in the recess is mounted the thermal flow sensor device or the assembly described above, with the electrically driven thermal element facing the channel.

Aspects also provide a method of manufacture of a thermal flow sensor device for sensing flow in a channel based on temperature measurements, the method having the steps of forming an electrically driven thermal element on a front side of the thermal flow sensor device arranged to face the channel, and forming a bond pad coupled electrically to the electrically driven thermal element, for making electrical contact off the thermal flow sensor device, the bond pad being arranged to face away from the front side to be accessible for contact from a backside of the thermal flow sensor device. These methods steps are compatible with a standard CMOS processing flow, which allows economical manufacture.

A conductive layer can be provided for electrical connection between the electrically driven thermal element and the bond pad, whereby the bond pad comprises a back side of the metal layer. When this layer is on the front side of the device it can help to improve the thermal response time along a direction parallel to the main direction of the fluid channel.

The thermal flow sensor device can have a substrate such as a semiconducting substrate, and the method can have the step of patterning the substrate to provide an aperture to expose the bond pad to enable contact with the bond pad through the aperture.

The method may also have the step of patterning the substrate to form a pillar, the step of forming the bond pad comprising forming the bond pad on the pillar.

The method may include the step of assembling the thermal flow sensor device onto a printed circuit board, and coupling the bond pad to a corresponding contact on the printed circuit board.

The thermal flow sensor device may be advantageously mounted into a recess in a wall of a channel for fluid flow.

Other aspects include sensors and sensor systems having such integrated circuits and methods of manufacturing such integrated circuits or such systems and methods of operating such sensors and sensor systems having such integrated circuits.

Aspects also provide a method of manufacture of a thermal flow sensor device, e.g. a thermal flow sensor integrated circuit for sensing flow in a fluid channel based on temperature measurements, comprising the steps of forming an electrically driven thermal, e.g. an element temperature sensing element on a front side of the integrated circuit arranged to face the fluid channel, and forming a bond pad coupled electrically to the electrically driven thermal element or the temperature sensing element, for making electrical contact off the integrated circuit, the bond pad being arranged to face away from the fluid channel.

The method can involve the step of forming the bond pad on a backside of a metal layer, or patterning a substrate to form an aperture, and forming the bond pad in the aperture, or patterning a substrate to form a pillar and forming the bond pad on the pillar.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detector for detecting falls of a user or an object to which the fall detector is attached, the fall detector comprising:
   an air flow channel;
   an air flow sensor disposed adjacent the air flow channel and configured to measure air flow along the air flow channel;
   an accelerometer configured to measure accelerations of the fall detector;
   a processor configured to:
     estimate an orientation of the fall detector from the measurements from the accelerometer,
     estimate a vertical velocity from the measurements from the air flow sensor and the estimated orientation,
     estimate a change in altitude from the estimated vertical velocity,
     determine whether a fall has occurred based on the estimated change in altitude.

2. The fall detector as claimed in claim 1, wherein the air flow sensor is a thermal air flow sensor.

3. The fall detector as claimed in claim 2, wherein the thermal air flow sensor senses air flow velocity in the air flow channel based on temperature measurements.

4. The fall detector as claimed in claim 1, further including:
   an alarm configured to be triggered by the processor when the processor determines that a fall has occurred.

5. A fall detector for detecting falls of a user or an object to which the fall detector is attached, the fall detector comprising:
   an air flow sensor configured to provide air flow measurements indicative of air flow velocity, the air flow sensor including:
     an air flow channel, the air flow measurements being indicative of an air flow velocity in the air flow channel,
     an electrically driven thermal element on a front side of the thermal air flow sensor arranged to face the air flow channel, and
     a bond pad coupled electrically to the electrically driven thermal element, the bond pad being arranged to face away from the front side to be accessible for contact from a backside of the air flow sensor, the air flow measurements being output via the bond pad,
   an accelerometer configured to measure accelerations of the fall detector; and
   a processor configured to process the air flow measurements from the bond pad and the thermal element and the acceleration measurements from the accelerometer to determine whether a fall has occurred.

6. The fall detector as claimed in claim 5, wherein the air flow sensor further includes:
   a conductive layer on the front side of the air flow sensor configured for electrical connection between the electrically driven thermal element and the bond pad, and the bond pad comprises a back side of the conductive layer.

7. The fall detector as claimed in claim 6, wherein the air flow sensor further includes:
an insulating layer configured to electrically insulate the air flow sensor from a fluid in the air flow channel.

8. The fall detector as claimed in claim 7, wherein the air flow sensor further includes:
a substrate, the substrate being patterned to provide an aperture to expose the bond pad to enable contact with the bond pad through the aperture.

9. The fall detector as claimed in claim 8, wherein the electrically driven thermal element includes:
a heating element and a temperature sensor element disposed on the front side of the air flow sensor facing the air flow channel.

10. The fall detector as claimed in claim 5, further including:
an alarm configured to be triggered by the processor when the processor determines that a fall has occurred.

11. A method in a fall detector of detecting falls of a user or an object to which the fall detector is attached, the method comprising:
with a thermal air flow sensor, which is disposed adjacent an air flow channel of the fall detector, measuring air flow along the air flow channel of the fall detector;
measuring accelerations of the fall detector with an accelerometer; and
with a processor,
estimating an orientation of the fall detector from the measurements from the accelerometer, estimating a vertical velocity from the measurements from the air flow sensor and the estimated orientation, estimating a change in altitude from the estimated vertical velocity, and determining whether a fail has occurred based on the estimated change in altitude.

12. The method as claimed in claim 11, further including:
with the processor, triggering an alarm when the processor determines that the fall has occurred.

13. A fall detector comprising:
an accelerometer configured to measure orientation and accelerations;
an air flow sensor configured to measure air flow through a channel; and
a processor configured to:
with the orientation measurements from the accelerometer, identify air flow measurement components in a vertical direction,
from the air flow measurement components in the vertical direction, generate a vertical velocity profile indicating how the velocity changes over time,
from the accelerations measured by the accelerometer, generating an acceleration profile which indicates timing and magnitude of impacts, and
determining whether a fall has taken place from the vertical velocity profile and the acceleration profile.

14. The fall detector as claimed in claim 13, further including:
an alarm configured to be triggered by the processor when the processor determines that a fall has occurred.

* * * * *